United States Patent [19]

Fauran et al.

[11] 3,951,968
[45] Apr. 20, 1976

[54] (2-6-OXYMETHYLENE) MORPHOLINO (4,3A) BENZIMIDAZOLES

[75] Inventors: Claude P. Fauran, Paris; Jeannine A. Eberle, Chatou; Michel J. Turin; Guy M. Raynaud, both of Paris; Claude J. Gouret, Meudon, all of France

[73] Assignee: Delalande S.A., Courbevoie, France

[22] Filed: Sept. 17, 1974

[21] Appl. No.: 506,825

[30] Foreign Application Priority Data
Oct. 3, 1973  France.............................. 73.35379

[52] U.S. Cl............................. 260/244 R; 424/248
[51] Int. Cl.²............... C07D 265/00; C07D 273/00; C07D 295/00
[58] Field of Search...................... 260/244; 424/248

[56] References Cited
UNITED STATES PATENTS
3,058,980   9/1962   Berg............................... 260/244 R Primary Examiner—Stanley J. Friedman
Assistant Examiner—D. W. Robinson
Attorney, Agent, or Firm—Woodhams, Blanchard and Flynn

[57] ABSTRACT

Compounds having the formula

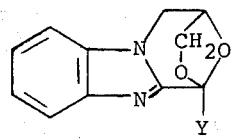

wherein Y is an aliphatic radical having up to 4 carbon atoms, phenyl, or phenyl substituted by one or more halogens, aliphatic radical having up to 4 carbon atoms, methoxy or trifluoromethyl.

The compounds are prepared by reacting epichlorohydrin with benzimidazole substituted at the 2 position by

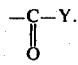

The compounds possess diuretic, sedative, antiulcerous, analgesic, antiinflammatory and cardiac analeptic properties.

8 Claims, No Drawings

(2-6-OXYMETHYLENE) MORPHOLINO (4,3A) BENZIMIDAZOLES

The present invention relates to novel (2,6-oxymethylene) morpholino (4,3a) benzimidazoles, their process of preparation and their therapeutic application.

The novel compounds according to the invention correspond to the general formula:

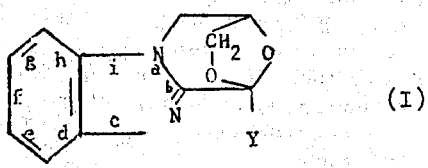

in which Y represents:
an alkyl radical containing up to 4 carbon atoms; or
a phenyl ring optionally substituted by one or more halogen atoms, by one or more alkyl radicals containing up to 4 carbon atoms or by one or more methoxy or trifluoromethyl radicals.

The process according to the invention consists in reacting epichlorhydrin of formula:

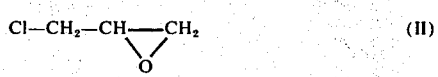

with a carbonyl derivative of benzimidazole corresponding to the general formula:

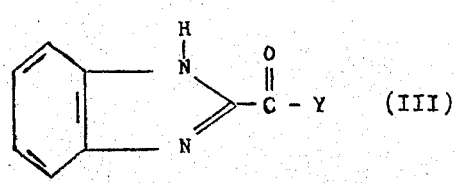

in which Y has the same significance as in the formula I.

The compounds of formula III are themselves novel and result from the oxidation of a hydroxyl derivative of benzimidazole of general formula:

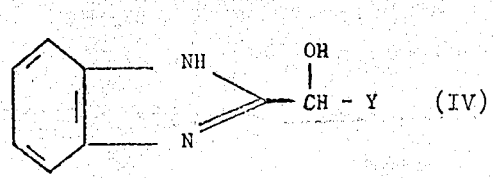

in which Y has the same significance as in formula I:

It is to be noted that the oxidation is effected with the aid of selenium oxide in an acetic medium.

The compounds of formula IV are also novel and are obtained by the cyclisation of orthophenylene diamine of formula:

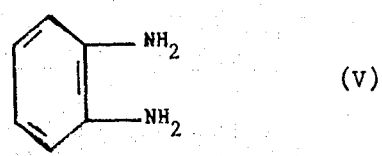

with an α-hydroxyl carboxylic acid of general formula:

in which Y has the same significance as in the general formula I:

The following preparation is given by way of example to illustrate the invention.

EXAMPLE (2,6-oxymethylene-2-phenyl) morpholino (4,3a) benzimidazole. (Code No. 72111)

1st stage: 2-phenylhydroxymethyl benzimidazole (Code No. 70242)

0.9 mol of mandelic acid is added to a solution of 0.6 mol of orthophenylene diamine in 600 ml of 4N hydrochloric acid. After reacting for 2 hours under reflux, the reaction mixture is taken up in 600 ml. of water and is neutralised with the aid of 6N ammonia. The crude product obtained is purified by recrystallisation from isopropyl alcohol.

| Melting point | = 211°C | | |
|---|---|---|---|
| Yield | = 53% | | |
| Empirical formula | = $C_{14}H_{12}N_2O$ | | |
| Elementary analysis: | C | H | N |
| Calculated (%) | 74.98 | 5.39 | 12.49 |
| Found (%) | 74.78 | 5.29 | 12.36 |

2nd stage: 2-benzoyl benzimidazole. (Code No. 70293)

0.09 mol of selenium oxide is added to a solution of 0.18 mol of 2-phenylhydroxymethyl benzimidazole obtained from the preceding stage in 220 ml of acetic acid. The mixture is maintained under reflux for 8 hours. The solution is then cooled. The mineral salts are removed from the mixture by filtration when warm. The filtrate is cooled and the 2-benzoyl benzimidazole precipitates out.

| Melting point | = 224°C | | |
|---|---|---|---|
| Yield | = 83% | | |
| Empirical formula | = $C_{14}H_{10}N_2O$ | | |
| Elementary analysis: | C | H | N |
| Calculated (%) | 75.66 | 4.54 | 12.61 |
| Found (%) | 75.83 | 4.47 | 12.56 |

3rd stage: (2,6-oxymethylene-2-phenyl)morpholino (4,3a) benzimidazole. (Code No. 72111)

A solution of sodium ethylate is prepared with the aid of 60 ml of ethanol and 0.05 gram. atom of sodium. After adding the 2-benzoyl benzimidazole obtained from the preceding stage thereto, 0.15 mol of epichlorhydrin is added over a period of 30 minutes, and then the reaction mixture is refluxed for 1 hour. The sodium chloride formed is removed by filtration. After evaporation of the ethanol the crude product obtained is purified by recrystallisation from isopropyl alcohol.

| Melting point | = 157°C | | |
|---|---|---|---|
| Yield | = 50% | | |
| Empirical formula | = $C_{17}H_{14}N_2O_2$ | | |
| Elementary analysis: | C | H | N |
| Calculated (%) | 73.36 | 5.07 | 10.07 |
| Found (%) | 73.24 | 5.09 | 10.21 |

The compounds of formula I listed in the following Table I have been prepared according to the mode of operation of the example The compounds of formulae III and IV listed in the following Tables II and III, have themselves been synthesised according to the mode of operation described in the second and in the first stages of the example, respectively.

TABLE I

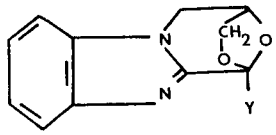

| Code No. | —Y | Empirical formula | Molecular weight | Melting point (°C) | Yield (%) | Calculated (%) C | H | N | Found (%) C | H | N |
|---|---|---|---|---|---|---|---|---|---|---|---|
| 71 433 | —$CH_3$ | $C_{12}H_{12}N_2O_2$ | 216.23 | 139 | 65 | 66.65 | 5.59 | 12.96 | 66.45 | 5.58 | 13.06 |
| 72 838 | —C₆H₄—Cl | $C_{17}H_{13}ClN_2O_2$ | 312.75 | 192 | 60 | 65.28 | 4.19 | 8.96 | 65.39 | 4.34 | 8.80 |
| 730220 | —C₆H₄—F | $C_{17}H_{13}FN_2O_2$ | 296.29 | 130 | 45 | 68.91 | 4.42 | 9.46 | 68.73 | 4.33 | 9.26 |
| 730222 | —C₆H₄—$CH_3$ | $C_{18}H_{16}N_2O_2$ | 292.32 | 189 | 44 | 73.95 | 5.52 | 9.58 | 74.11 | 5.42 | 9.78 |
| 730212 | —C₆H₄—$OCH_3$ | $C_{18}H_{16}N_2O_3$ | 308.32 | 196 | 32 | 70.11 | 5.23 | 9.09 | 69.99 | 5.43 | 8.99 |
| 730287 | —C₆H₄—$CF_3$ | $C_{18}H_{13}F_3N_2O_2$ | 346.30 | 131 | 46 | 62.43 | 3.78 | 8.09 | 62.18 | 3.89 | 8.08 |

TABLE II

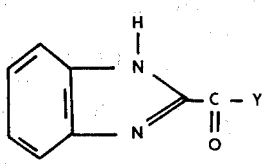

formula III

| Code NO. | —Y | Empirical formula | Molecular weight | Melting point (°C) | Yield (%) | Calculated (%) C | H | N | Found (%) C | H | N |
|---|---|---|---|---|---|---|---|---|---|---|---|
| 72 814 | —⟨⟩—F | $C_{14}H_9FN_2O$ | 240.22 | 213 | 89 | 69.99 | 3.78 | 11.66 | 69.88 | 4.02 | 11.50 |
| 730152 | —⟨⟩—CH₃ | $C_{15}H_{12}N_2O$ | 236.16 | 258 | 78 | 76.25 | 5.12 | 11.86 | 75.97 | 5.13 | 11.56 |
| 730172 | —⟨⟩—OCH₃ | $C_{15}H_{12}N_2O_2$ | 252.26 | 194 | 82 | 71.41 | 4.80 | 11.11 | 71.27 | 4.56 | 10.93 |
| 730186 | —⟨⟩(CF₃) | $C_{15}H_9F_3N_2O$ | 290.24 | 206 | 62 | 62.07 | 3.13 | 9.65 | 62.14 | 3.05 | 9.50 |

TABLE III

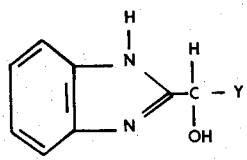

formula IV

| Code No. | —Y | Empirical formula | Molecular weight | Melting point (°C) | Yield (%) | Calculated (%) C | H | N | Found (%) C | H | N |
|---|---|---|---|---|---|---|---|---|---|---|---|
| 72 731 | —⟨⟩—F | $C_{14}H_{11}FN_2O$ | 242.24 | 135 | 52 | 69.41 | 4.58 | 11.57 | 69.41 | 4.69 | 11.69 |
| 730132 | —⟨⟩—CH₃ | $C_{15}H_{14}N_2O$ | 238.28 | 151 | 66 | 75.60 | 5.92 | 11.76 | 75.54 | 5.67 | 11.86 |
| 730183 | —⟨⟩—OCH₃ | $C_{15}H_{14}N_2O_2$ | 254.28 | 155 | 45 | 70.85 | 5.55 | 11.02 | 70.52 | 5.78 | 10.99 |
| 730168 | —⟨⟩(CF₃) | $C_{15}H_{11}F_3N_2O$ | 292.25 | 168 | 72 | 61.64 | 3.79 | 9.59 | 61.48 | 3.70 | 9.58 |

The compounds of general formula I have been tested on animals in the laboratory and have been shown to posses diuretic, sedative, antiulcerous, analgesic, antiinflammatory and cardiac analeptic properties.

1. Diuretic properties

The compounds of formula I, administered by oral means to the mouse, simultaneously with a volume of 1 ml of an isotonic solution of sodium chloride per 25 g of the corporeal weight of the mouse, are capable of provoking an augmentation of the volume of urine emitted by reference to control animals, the volume being measured for 6 hours following administration.

Thus, the administration of 25 mg/kg/p.o. of the compound of Code No. 71433 produces an augmentation of urinary elimination by 40%.

2. Sedative properties

The compounds of formula I, administered by oral means to the mouse, reduce the number of explorations in the escape enclosure.

By way of example, the following Table IV lists the percentage reduction in the number of explorations in the escape enclosure following the administration of 100 mg/kg/p.o of different compounds of formula I to the mouse.

TABLE IV

| Code No. of compound tested | Percentage reduction in number of explorations in an escape enclosure - (%) |
|---|---|
| 72 111 | 30 |
| 730 220 | 25 |

3. Antiulcerous properties

The compounds of formula I, administered by oral means, reduce the extend of gastric ulcers provoked in a rat by tying of the pylorus (Shay ulcers).

By way of example, the following Table V lists the percentage reduction in the Shay ulcers obtained following the administration of 50 mg/kg/i.d. of different compounds of formula I.

TABLE V

| Code No. of compound tested | Percentage reductions of Shay ulcers (%) |
|---|---|
| 72 111 | 30 |
| 72 838 | 35 |
| 730 212 | 40 |
| 730 222 | 35 |
| 730 287 | 32 |

4. Analgesic properties

The compounds of formula I, administered by oral means to the mouse, are capable of reducing the number of painful stretchings caused by the intraperitoneal injection of acetic acid.

By way of example, the following Table VI lists the percentage diminution in the number of painful stretchings caused by the intraperitoneal injection of acetic acid, by the administration of 100 mg/kg/p.o. of different compounds of formula I.

TABLE VI

| Code No. of compound tested | Percentage diminution in number of painful stretchings - (%) |
|---|---|
| 72 111 | 75 |
| 72 838 | 60 |
| 730 212 | 65 |
| 730 220 | 60 |
| 730 222 | 60 |
| 730 287 | 60 |

5. Antiinflammatory properties

These properties are shown by a diminution of the local oedema caused by the sub-plantar injection of a phlogogenic agent such as carraghenine, in the rat following the oral admininstration of compounds of formula I.

Thus, the administration of 100 mg/kg/p.o. of the compound of Code No. 72111 produces a diminution of 70% of the oedema provoked by the sub-plantar injection of carraghenine.

6. Cardiac analeptic properties

These properties are shown by an augmentation of the force of contractions (positive inotrope action) on the isolated heart of a guinea pig, maintained in a conserving medium and under appropriate experimental conditions.

Thus, a positive inotrope action is observed on the isolated heart of a guinea-pig using a concentration of the compound of Code No. 730287 of 1 $\mu$g/ml in the conserving medium.

As a result of a comparison between the lethal doses listed in the following TAble VII and the pharmacologically-active doses mentioned above, the difference between the said doses is sufficiently great to permit the utilisation of the compounds of formula I in therapeutics.

TABLE VII

| Code No. of compound tested | Dose administered (mg/kg/p.o.) | Percentage mortality (%) |
|---|---|---|
| 71 433 | 1 650 | ≃ 50 |
| 72 111 | 1 850 | ≃ 50 |
| 72 838 | 2 000 | 10 |
| 730 212 | 2 000 | 0 |
| 730 220 | 1 600 | ≃ 50 |
| 730 222 | 2 000 | 10 |
| 730 287 | 2 000 | 0 |

The compounds of formula I are useful in the treatment of cardiac insufficiencies, oedemas, anxieties, inflammatory pains and diverse originating pains, and gastro-duodenal ulcers.

They may be administered by oral means in the form of tablets, gelules and dragees containing 50 to 250 mg of active ingredient (1 to 6 times a day), in the form of suspensions containing 0.5 to 2% of active ingredient (20 to 60 drops, 1 to 4 times a day), by parenteral means in the form of injectable ampoules containing 10 to 100 mg of active ingredient (1 to 3 times a day) and by rectal means in the form of suppositories containing 25 to 250 mg of active ingredient (1 to 3 times a day).

Accordingly, the present invention also relates to a therapeutic composition comprising a compound of the general formula I together with a therapeutically acceptable carrier.

What we claim is:

1. A compound having the formula

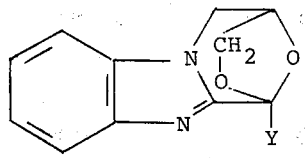

wherein Y is alkyl having one to 4 carbon atoms, phenyl, or phenyl substituted by at least one substituent selected from the group consisting of halogen, alkyl containing one to 4 carbon atoms, methoxy and trifluoromethyl.

2. A compound as claimed in claim 1 in which Y is phenyl.

3. A compound as claimed in claim 1 in which Y is methyl.
4. A compound as claimed in claim 1 in which Y is 4-chlorophenyl.
5. A compound as claimed in claim 1 in which Y is 4-fluorophenyl.
6. A compound as claimed in claim 1 in which Y is 4-methylphenyl.
7. A compound as claimed in claim 1 in which Y is 4-methoxyphenyl.
8. A compound as claimed in claim 1 in which Y is 3-trifluoromethylphenyl.

* * * * *